US008894612B2

(12) United States Patent
Hawkins et al.

(10) Patent No.: US 8,894,612 B2
(45) Date of Patent: Nov. 25, 2014

(54) DISPOSABLE INFUSION DEVICE FILLING APPARATUS AND METHOD

(71) Applicant: Calibra Medical, Inc., Redwood City, CA (US)

(72) Inventors: Daniel Hawkins Hawkins, Newcastle, WA (US); Brett J. Carter, Monroe, WA (US); John M. Adams, Kirkland, WA (US)

(73) Assignee: Calibra Medical, Inc., Redwood City, CA (US)

( * ) Notice: Subject to any disclaimer, the term of this patent is extended or adjusted under 35 U.S.C. 154(b) by 0 days.

(21) Appl. No.: 13/854,189

(22) Filed: Apr. 1, 2013

(65) Prior Publication Data
US 2013/0226092 A1 Aug. 29, 2013

Related U.S. Application Data

(60) Continuation of application No. 13/024,618, filed on Feb. 10, 2011, now Pat. No. 8,409,151, which is a division of application No. 11/604,166, filed on Nov. 22, 2006, now Pat. No. 7,938,801.

(51) Int. Cl.
A61M 37/00 (2006.01)
A61M 5/142 (2006.01)
A61M 5/158 (2006.01)

(52) U.S. Cl.
CPC ............ *A61M 5/158* (2013.01); *A61M 5/14248* (2013.01); *A61M 2209/045* (2013.01); *A61M 2005/1585* (2013.01); *A61M 2205/583* (2013.01)
USPC ............................ 604/131; 604/151; 604/180

(58) Field of Classification Search
CPC ................... A61M 5/14248; A61M 2209/045; A61M 5/14244; A61J 1/2096
USPC ............................... 604/131, 151, 180, 890.1
See application file for complete search history.

(56) References Cited

U.S. PATENT DOCUMENTS

| 5,656,032 | A | 8/1997 | Kriesell |
| 5,776,103 | A | 7/1998 | Kriesel |
| 6,186,982 | B1 * | 2/2001 | Gross et al. .................... 604/132 |
| 6,293,159 | B1 * | 9/2001 | Kriesel et al. ............... 73/861.47 |
| 6,355,019 | B1 * | 3/2002 | Kriesel et al. ................. 604/132 |
| 6,537,249 | B2 | 3/2003 | Kriesell |
| 6,723,068 | B2 * | 4/2004 | Lavi et al. ....................... 604/82 |
| 6,786,244 | B1 | 9/2004 | Jones |
| 2002/0022855 | A1 | 2/2002 | Bobroff et al. |

(Continued)

OTHER PUBLICATIONS

International Search Report for International Patent Application No. PCT/US2007/024278, dated Apr. 7, 2008.

*Primary Examiner* — Nicholas Lucchesi
*Assistant Examiner* — Gerald Landry, II

(57) ABSTRACT

An infusion system includes a disposable wearable infusion device and a filler device. The disposable infusion device has a body arranged to be adhered to a patient's skin and a reservoir for holding a liquid medicant to be infused into the patient. The filler device is arranged to detachably receive the infusion device body and to transfer a volume of the liquid medicant to the infusion device reservoir. The filler device may be part of a service device arranged to detachably receive the infusion device and which also includes a cannula driver and a cannula for providing the infusion device with a cannula and deploying the cannula to beneath a patient's skin.

7 Claims, 6 Drawing Sheets

(56) References Cited

U.S. PATENT DOCUMENTS

| | | |
|---|---|---|
| 2002/0177819 A1* | 11/2002 | Barker et al. ............... 604/232 |
| 2003/0088238 A1 | 5/2003 | Pulsen et al. |
| 2003/0097093 A1* | 5/2003 | Navelier et al. ............. 604/68 |
| 2003/0105430 A1 | 6/2003 | Lavi et al. |
| 2003/0135159 A1 | 7/2003 | Daily et al. |
| 2004/0133166 A1* | 7/2004 | Moberg et al. ............. 604/151 |
| 2004/0138612 A1 | 7/2004 | Shermer et al. |
| 2004/0143216 A1 | 7/2004 | Douglas et al. |
| 2004/0158207 A1 | 8/2004 | Hunn et al. |
| 2004/0204687 A1 | 10/2004 | Mogensen et al. |
| 2005/0107743 A1 | 5/2005 | Fangrow |
| 2005/0203461 A1* | 9/2005 | Flaherty et al. ............. 604/131 |
| 2006/0129090 A1 | 6/2006 | Moberg et al. |
| 2006/0183984 A1 | 8/2006 | Dobbles |
| 2006/0200112 A1 | 9/2006 | Paul |
| 2007/0066939 A1 | 3/2007 | Krulevitch et al. |
| 2007/0106218 A1 | 5/2007 | Yodfat et al. |
| 2007/0233001 A1 | 10/2007 | Burroughs et al. |
| 2007/0250008 A1* | 10/2007 | Gelblum ..................... 604/151 |
| 2008/0097327 A1* | 4/2008 | Bente et al. ................. 604/155 |

* cited by examiner

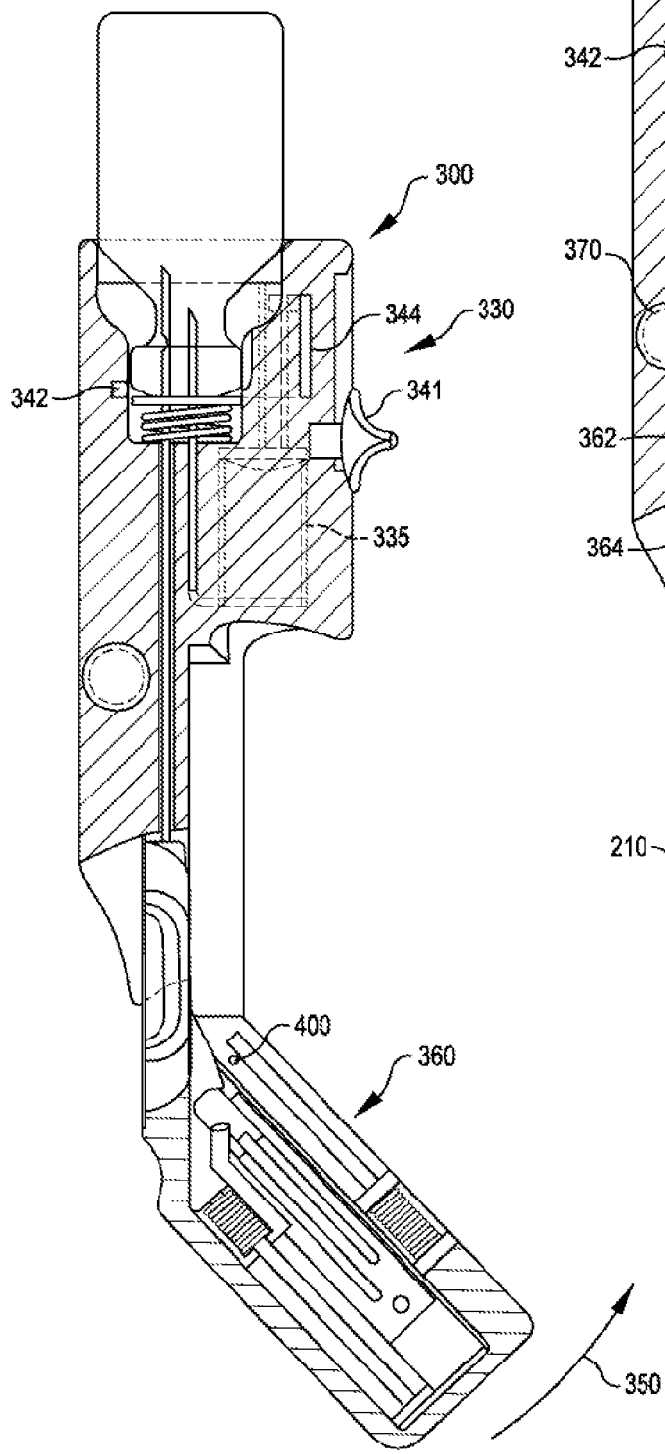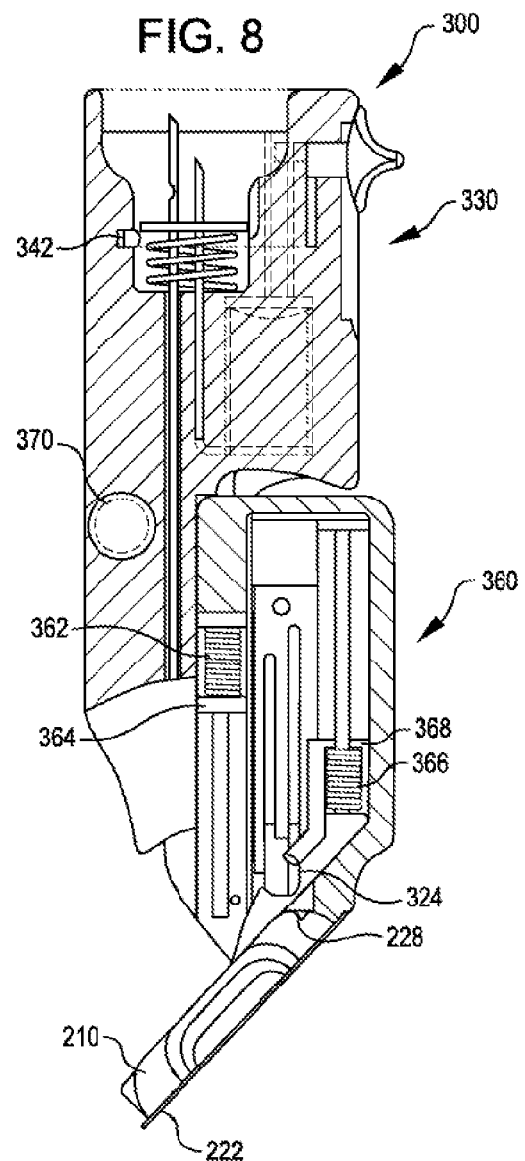

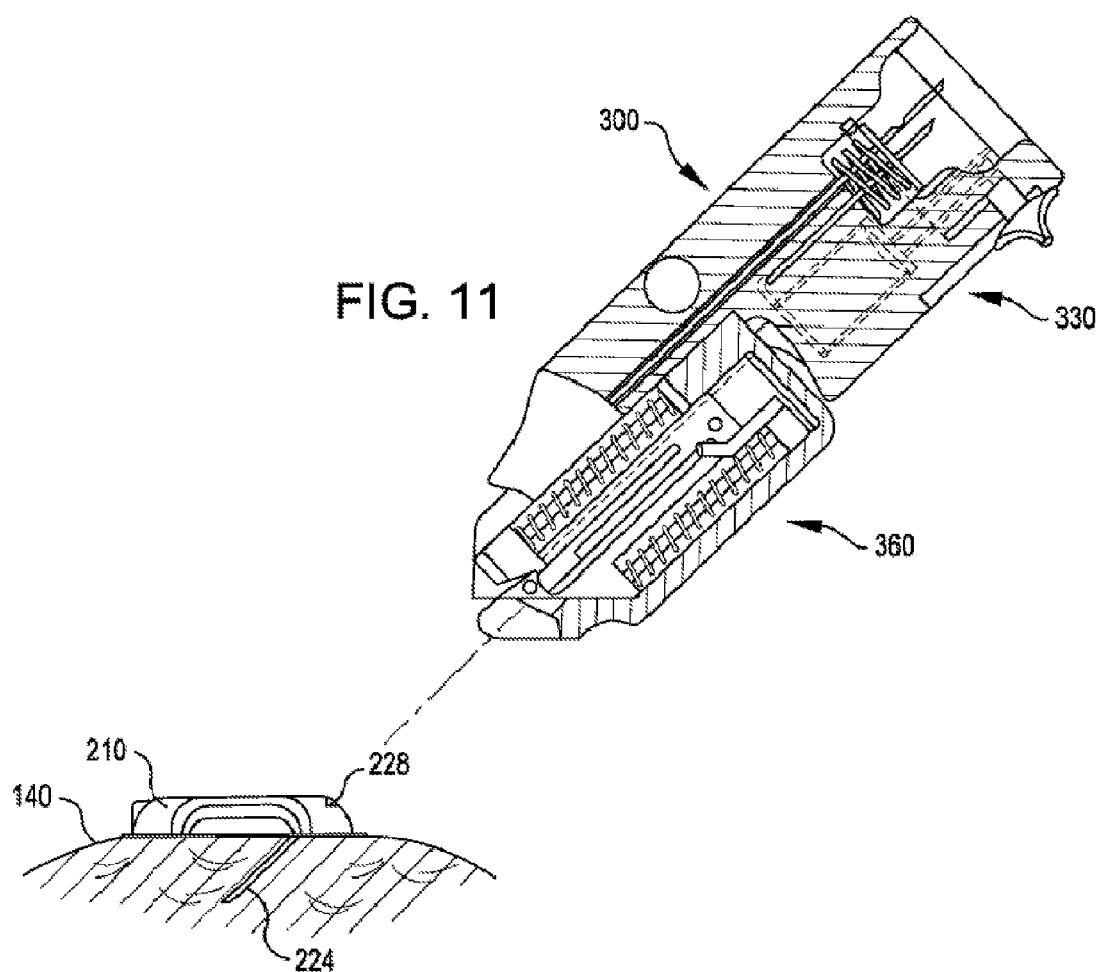

8,894,612 B2

DISPOSABLE INFUSION DEVICE FILLING APPARATUS AND METHOD

CROSS REFERENCE TO RELATED APPLICATIONS

This application is a continuation application of U.S. patent Divisional application Ser. No. 13/024,618, filed Feb. 10, 2011, which claims priority to U.S. Non-Provisional application Ser. No. 11/604,166, filed Nov. 22, 2006, allowed on May 10, 2011, all applications are herein incorporated by reference in their entireties.

BACKGROUND OF THE INVENTION

Tight control over the delivery of insulin in both type I diabetes (usually juvenile onset) and type II diabetes (usually late adult onset), has been shown to improve the quality of life as well as the general health of these patients. Insulin delivery has been dominated by subcutaneous injections of both long acting insulin to cover the basal needs of the patient and by short acting insulin to compensate for meals and snacks. Recently, the development of electronic, external insulin infusion pumps has allowed the continuous infusion of fast acting insulin for the maintenance of the basal needs as well as the compensatory doses (boluses) for meals and snacks. These infusion systems have shown to improve control of blood glucose levels. However, they suffer the drawbacks of size, cost, and complexity. For example, these pumps are electronically controlled and must be programmed to supply the desired amounts of basal and bolus insulin. This prevents many patients from accepting this technology over the standard subcutaneous injections.

Hence, there is a need in the art for a convenient form of insulin treatment which does not require significant programming or technical skills to implement to service both basal and bolus needs. Preferably, such a treatment would be carried out by an infusion device that is simple to use and mechanically driven negating the need for batteries and the like. It would also be preferable if the infusion device could be directly attached to the body and not require any electronics to program the delivery rates. The insulin is preferably delivered through a small, thin-walled tubing (cannula) through the skin into the subcutaneous tissue similar to technologies in the prior art.

While the idea of such a simple insulin delivery device is compelling, many obstacles must be overcome before such a device may become a practical realty. One problem resides in insulin supply. Patients vary greatly on the amount of insulin such a device must carry to provide treatment over a fixed time period of, for example, three days. This is one environment where one size does not fit all. Another problem is with cannula deployment to support insulin delivery. Cannula deployment to support delivery of the insulin beneath the patient's skin must be made easy and convenient. This is not as easy as it seems because cannula deployment, as generally and currently performed in the art, requires insertion of a cannula carrying needle into the patient and then retraction of only the needle to leave the cannula in place beneath the patient's skin. As will be seen subsequently, the present invention addresses these and other issues toward providing a simple, practical, and reliable insulin delivery device.

SUMMARY OF THE INVENTION

The invention provides an infusion system comprising a disposable wearable infusion device having a body arranged to be adhered to a patient's skin and a reservoir for holding a liquid medicant to be infused into the patient. The system further comprises a filler device arranged to detachably receive the infusion device body and transfer a volume of the liquid medicant to the infusion device reservoir.

The filler device may have a window through which the liquid medicant within the reservoir may be observed. This enables trapped air to be viewed and removed.

The filler device may have a cavity for receiving a vial of the liquid medicant, and establishes fluid communication between the infusion device reservoir and the liquid medicant upon concurrently receiving the infusion device body and the vial of liquid medicant. The filler device may arranged to transfer a desired volume of the liquid medicant from the vial to the infusion device reservoir. The filler may, for example, be arranged to meter a predetermined volume of medicant from the vial to the reservoir.

The filler device is preferably enabled to transfer a volume of the liquid medicant to the infusion device reservoir upon the cavity receiving the vial of the liquid medicant. The filler may further includes a pump that transfers the liquid medicant from the vial to the infusion device reservoir. The pump may be arranged to pump air into the vial to displace liquid medicant from the vial and into the reservoir. The filler may include a vent that vents the vial to atmospheric pressure when being received in the cavity. The filler cavity may seal the vial after the vent vents the vial to atmosphere as the cavity receives the vial.

The invention further provides a method comprising the steps of providing a disposable infusion device adapted to adhere to a patient's skin and having a reservoir for holding a liquid medicant to be infused into the patient, filling the reservoir at least partially with the liquid medicant, adhering the device to the patient's skin, and deploying a cannula through the device to beneath the skin of the patient The filling step may be performed before the adhering step is performed. The method may further include the step of pre-selecting a desired amount of the liquid medicant to be filled into the reservoir before filling the reservoir. The filling step may comprise the further step of detachably joining the device to a filler and providing the filler with a vial of the liquid medicant. The filling step may further comprise pumping liquid medicant from the vial into the reservoir. The pumping step may comprise admitting air into the vial to force liquid medicant from the vial into the reservoir. The filling step may further comprise venting the vial to atmospheric pressure before admitting the air into the vial. The filling step may include pre-selecting a desired amount of air to be admitted into the vial before admitting the air into the vial. The method may further include the step of removing air trapped in the reservoir after the reservoir is filled with the liquid medicant.

The method may include the further step of detaching the infusion device from the filler prior to adhering the device to the patient's skin. The deploying step may comprise detachably joining the infusion device to a cannula driver containing the cannula and driving the cannula from the cannula driver through the infusion device. The method may still further include the step of detaching the cannula driver from the infusion device after the cannula is deployed.

The method may further comprise the step of detachably joining the infusion device to a service device having a liquid medicant filler and the cannula to be deployed. The filling step may then further include inserting a vial of liquid medicant into the filling device from which the reservoir is to be filled. The adhering step may be performed with the service device joined to the infusion device and the deploying step may comprise driving the cannula from the service device through the infusion device. The service device may then be detached from the infusion device after the cannula is deployed.

In another embodiment, an infusion system comprises a disposable wearable infusion device having a body arranged to be adhered to a patient's skin and a reservoir for holding a liquid medicant to be infused into the patient, and a service device arranged to detachably receive the infusion device body. The service device has a filler that provides the infusion device reservoir with the liquid medicant and a cannula driver including a cannula arranged to drive the cannula into a deployed position extending from the infusion device to beneath the patient's skin.

In another embodiment, a filler device for filling a reservoir of a disposable wearable infusion device with a liquid medicant comprises a body arranged to detachably receive the infusion device and having a cavity for receiving a vial of the liquid medicant, a conduit that establishes fluid communication between the infusion device reservoir and the liquid medicant, and a pump that transfers a volume of the liquid medicant from the vial to the infusion device reservoir.

In a further embodiment, a service device for use with a disposable wearable infusion device having a reservoir for holding a liquid medicant to be infused into a patient comprises a body arranged to detachably receive the infusion device and having a cavity for receiving a vial of the liquid medicant, a filler that provides the infusion device reservoir with a volume of the liquid medicant from the vial, and a cannula driver including a cannula. The cannula driver is arranged to drive the cannula into a deployed position extending from the infusion device to beneath the patient's skin.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

FIG. 7 is a side view, with portions cut away, of the service device of FIG. 4 after having provided the infusion device with a desired quantity of the liquid medicant from the vial;

FIG. 8 is a side view, with portions cut away, of the service device of FIG. 4 after having been placed in a cannula drive configuration to an enable a cannula driver in accordance with an embodiment of the present invention;

FIG. 11 is a side view, with portions cut away, of the service device of FIG. 4 after the infusion device and the service device are separated leaving the infusion device deployed on the skin of the patient with the cannula extending beneath the patient's skin in a deployed position to deliver the liquid medicant to the patient.

DETAILED DESCRIPTION OF THE INVENTION

Figure 1:
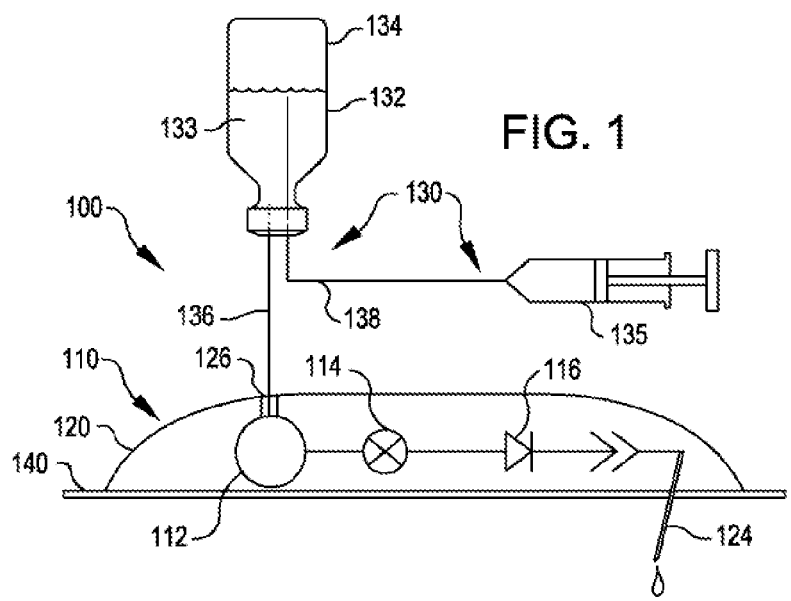
FIG. 1 is a schematic representation of a reservoir within a disposable wearable diffusion device being filled with a liquid medicant according to an embodiment of the present invention.

Referring now to FIG. 1, it is a schematic representation of an infusion system embodying the present invention. The system 100 generally includes a disposable wearable infusion device 110 and a filler 130. The filler 130 is seen in FIG. 1. filling a reservoir 112 within the diffusion device 110 with a measured quantity of a liquid medicant, such insulin, for example, according to an embodiment of the present invention.

The device 110 includes a body or enclosure 120 that is adhered to the skin 140 of a patient and that encloses the reservoir 112. The device 130 further includes a cannula 124 deployed from the device 110 to beneath the skin 140 of a patient to deliver the liquid medicant. The reservoir 112 is coupled to the cannula 124 by a pump 114 and a one-way check valve 116. Actuation of the pump provides a fixed quantity of the medicant to the cannula.

The filler 130 is adapted to receive a vial 132 of the liquid medicant 133. A first conduit 136 provides fluid communication from the vial 132, through a filling port septum 126, and into the reservoir 112. A second conduit 138 provides fluid communication from a pump 135 to the vial. The pump 135 is employed to pump air into the vial 132 to displace a known quantity of the liquid medicant 133 from the vial 132. The medicant is then delivered to the reservoir through the first conduit 136. As will be seen subsequently, and in accordance with one aspect of the present invention, as the vial 132 is received by the filler 130, the interior space 134 within the vial 132 is vented to atmospheric pressure and then sealed. This venting of the vial 132 assures that a known volume of air being pumped into the vial will displace a like volume of medicant for filling the reservoir.

Once the reservoir 112 is filled with a desired quantity of liquid medicant, the infusion device may be adhered to the patient's skin 140. Preferably thereafter, the cannula 124 is deployed.

Figure 2:
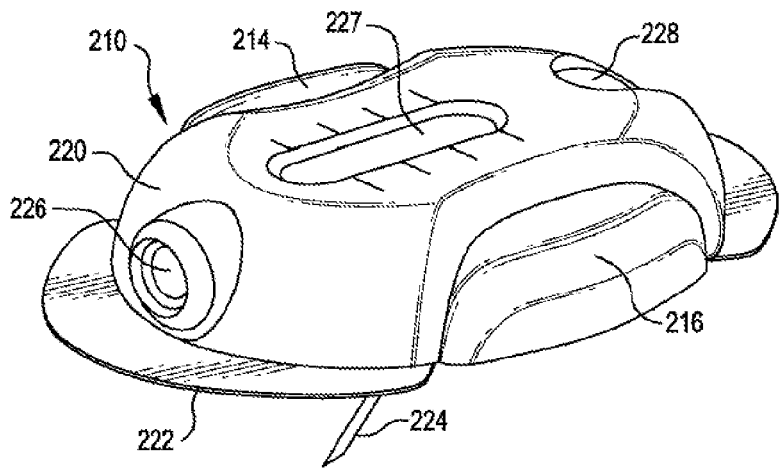
FIG. 2 is perspective view of an infusion device embodying the present invention.
Figure 3:
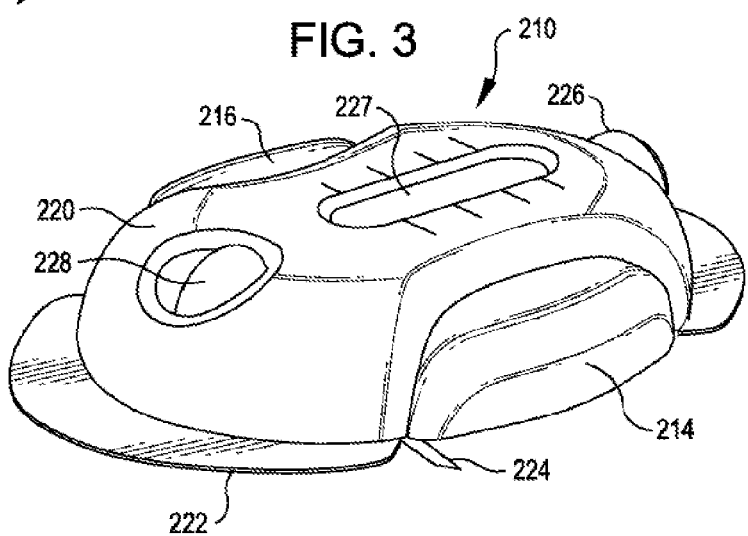
FIG. 3 is a perspective view of the device of FIG. 2 with the device rotated 180 degrees.

Referring now to FIG. 2, it is perspective view of an infusion device 210 embodying the present invention. FIG. 3 is a perspective view of the device 210 after being rotated 180 degrees. The device 210 includes an enclosure 220 and a base 222. The device 210 further includes a pair of actuator buttons 214 and 216 which, when concurrently depressed, cause a fixed quantity of liquid medicant to be dispensed from a cannula 224. The device 210 further includes a filler port septum 226 through which the reservoir (not shown) is filled and a viewing window 227 through which the liquid medicant may be viewed during the filling process. More particularly, the viewing window provides a means by which air bubbles within the reservoir may be seen to facilitate removal thereof. Lastly, as may be seen in FIGS. 2 and 3, the device 210 includes an auxiliary port septum 228. The port septum 228 is provided to enable deployment of the cannula 224 in a manner as described subsequently and to receive boluses of liquid medicant, such as basal or long acting insulin, to be dispensed through the cannula 224.

Figure 4:
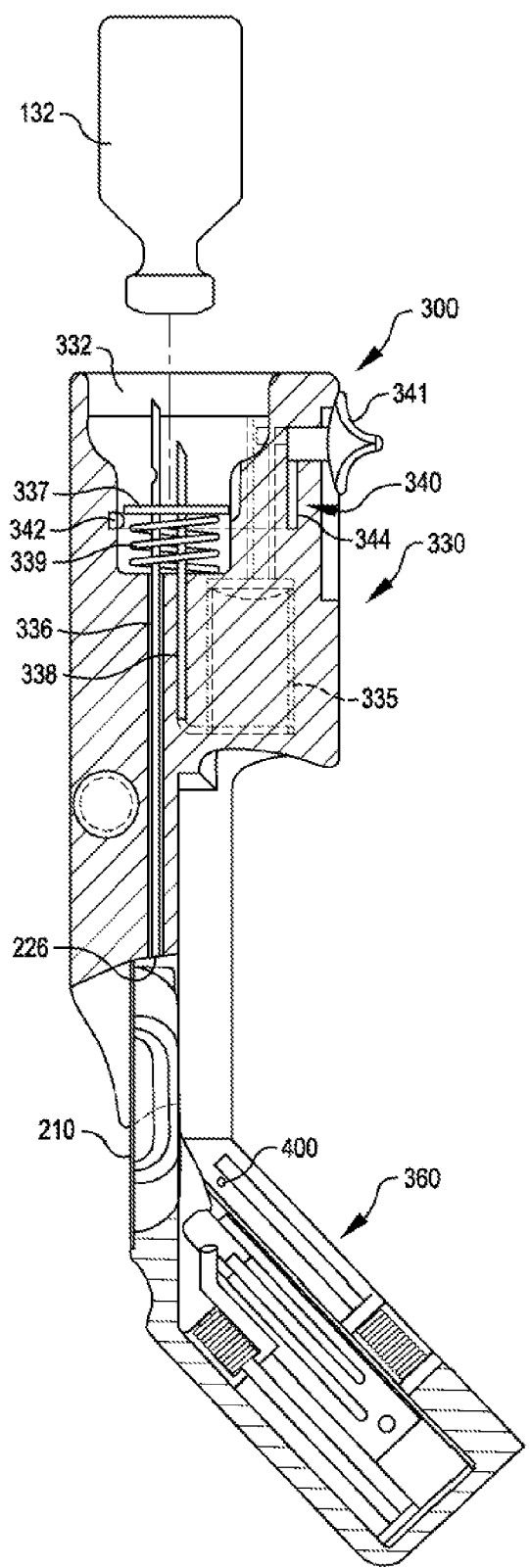
FIG. 4 is a side view, with portions cut away, of a service device embodying the present invention with an infusion device detachably received therein and about to receive a vial of liquid medicant.

FIG. 4 is a side view, with portions cut away, of a service device 300 embodying the present invention with the infusion device 210 detachably received therein. The service device includes a filler device 330 and a cannula driver 360. The filler device 330 and cannula driver 360, for reasons which will become apparent herein after, are pivotally connected at a pivot point 400.

As seen in FIG. 4, the filler device 330 is about to receive a vial 132 of liquid medicant. The filler device 330 includes a cavity 332 for receiving the vial 132. The filler device 330 further includes a first conduit 336 and a second conduit 338. As described in connection with FIG. 1, the first conduit 336 serves to provide fluid communication between the vial 132 and the reservoir (not shown) of the infusion device 210 to be filled. The second conduit 338 provides fluid communication between the pump 335 within the filler device 330 and the vial 132. The first conduit 336 is carried on a stop 337 which is spring loaded by a spring 339. As will be seen subsequently, when the vial 132 engages stop 339, further movement of the vial into the cavity 332 will cause the first conduit 336 to travel with the stop 339 and vial 132 forcing the end of the first conduit 336 into the filling port septum 226.

The filler device 330 also includes an interlock 340 that prevents the pump arm from being displaced and thus premature actuation thereof before the vial 132 is fully received within the cavity. Hence, the filler device is enabled to transfer a volume of the liquid medicant to the infusion device reservoir only upon the cavity 332 fully receiving the vial 132. To that in end, the interlock 340 includes a follower 342 and an inter-connected latch 344. As shown in FIG. 4, the latch 344 prevents the arm 341 from being displaced. However, when the vial is received into the cavity 332, the follower engages the vial 132 and is displaced causing the latch to be pulled free of the arm 341. This operation will be seen more clearly herein after.

Figure 5:
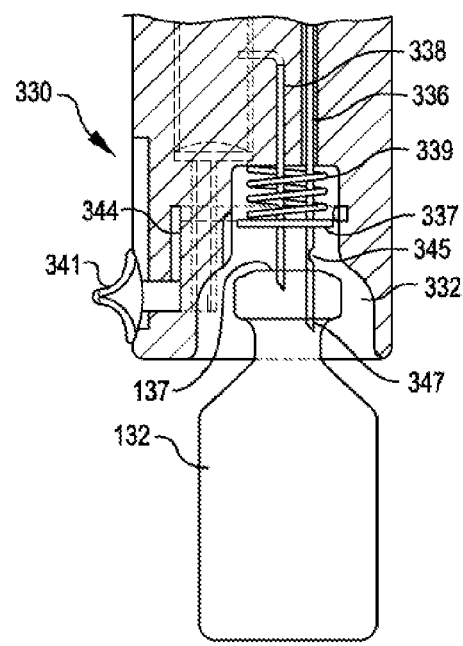
FIG. 5 is side view, with portions cut away, of the service device of FIG. 4 after having partially received the vial of liquid medicant for venting the interior of the vial to atmospheric pressure in accordance with an embodiment of the present invention.

FIG. 5 shows how the vial 132 may be vented as it is received into the cavity of the filler device 330. In FIG. 5 it may be seen that the vial 132 has a sealing membrane 137. Also, it may be seen that the first conduit 226 includes an opening 345 displaced from the end 347 of the first conduit 336. To vent the vial 132, the vial 132 and the filler device 330 are inverted as illustrated. When the vial 132 is advanced to cause the membrane to be pierced by the end 347 of the first conduit 336, the vial 132 is vented to atmospheric pressure as long as the membrane 137 is between the end 347 and the opening 345 of the first conduit 336.

Figure 6:
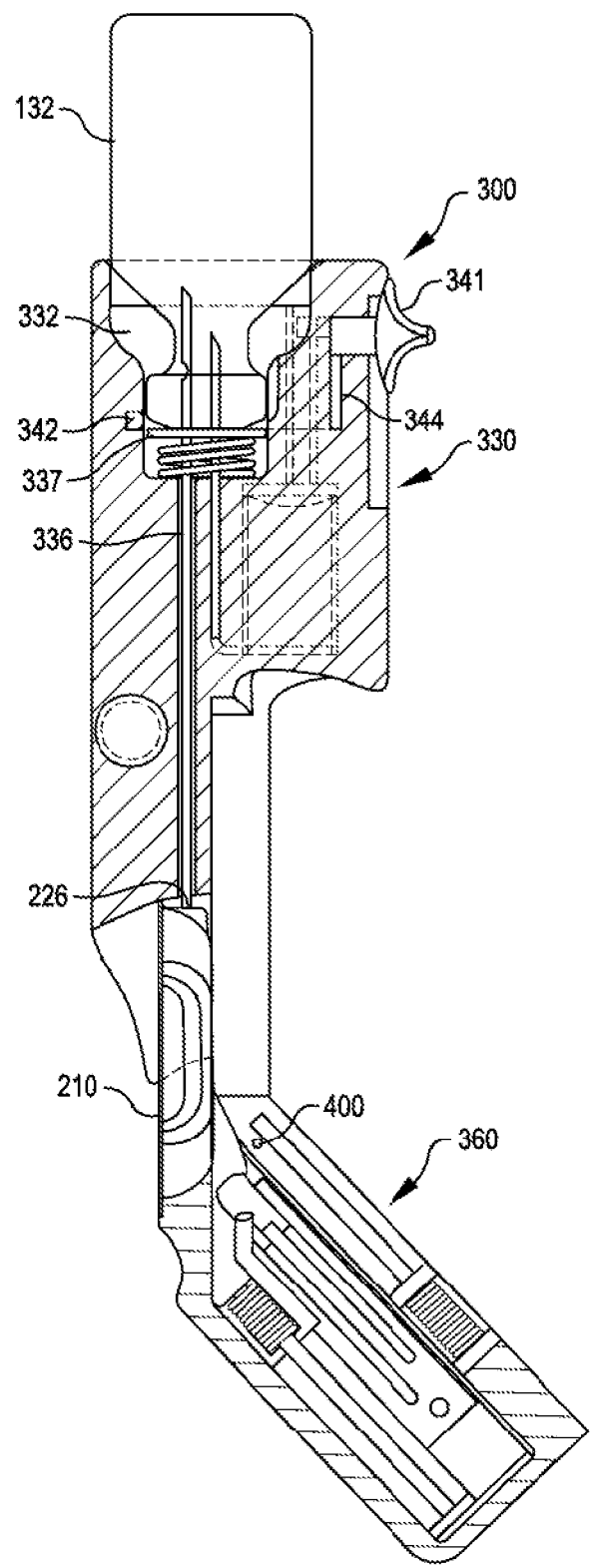
FIG. 6 is a side view, with portions cut away, of the service device of FIG. 4 after having fully received the vial of liquid medicant to establish fluid communication between the vial and the infusion device in accordance with an embodiment of the present invention.

FIG. 6 shows the vial 132 fully received within the cavity 332 of the filler device 330. The follower 342 has been displaced by its engagement with the vial 132 to cause the latch 344 to be moved clear of the arm 341. Also, the first conduit 336 has entered the filling port septum 226 of the infusion device 210 after having traveled with the stop 337 and the vial 132. The infusion device 210 is now ready to be filled with a quantity of liquid medicant from the vial 132.

FIG. 7 shows the filler device 330 after having filled the infusion device 210 with a quantity of liquid medicant. The quantity of liquid medicant filled depends upon the length of travel of the arm 341 and hence the amount of air pumped into the vial 132 by the pump 335. In this manner, the quantity of liquid medicant filled may be accurately preselected and metered. Further, after the liquid medicant has been transferred to the infusion device 210, the medicant may be viewed through the window 227 (FIGS. 2 and 3) for air bubbles. Any observed air bubbles may be eliminated by dithering the arm 341 back and forth. This dithering of arm 341 will cause air trapped in the reservoir to be returned to the vial 132 and then returned to the reservoir. The amount of air returned to the reservoir each time is less than the amount of air previously removed from the reservoir. Hence, in this manner, the air trapped in the reservoir may be removed.

After the filling process is completed, the vial 132 may be removed from the service device 300. Then, the cannula driver 360 is pivoted about pivot point 400 in the direction of arrow 350 (FIG. 7) and locked in the position shown in FIG. 8. With the cannula driver 360 locked in the position shown in FIG. 8, it is now in a cannula drive configuration. This results in a cannula/needle assembly 324 to be aligned with the auxiliary port septum 228 of the infusion device 210. The base 222 of the infusion device 210 may now be adhered to the patient's skin.

As will be seen subsequently, a first drive element 362 may now be released to drive the cannula/needle assembly 324 through the port septum 228 rendering the cannula 224 in a deployed position (FIG. 9) A second drive element 366 may thereafter be released to withdraw only the needle 225 back into the driver 360 leaving the cannula 224 in its deployed position and the needle safely tucked away for sharps disposal.

With further reference to FIG. 8, the first drive element comprises a spring. The spring 362 is coupled to a follower 364. The spring 362 may be released by the concurrent depression of a pair of aligned actuator buttons on opposite sides of the driver 360. One such actuator button 370 is shown in the FIG. 8. Preferably the actuator buttons are only coupled to release the springs 362 and 366 when the driver 360 is locked in the cannula drive configuration. Hence, in this manner, the driver is enabled only when the driver is properly positioned and locked for the purpose of deploying the cannula 224.

Figure 9:
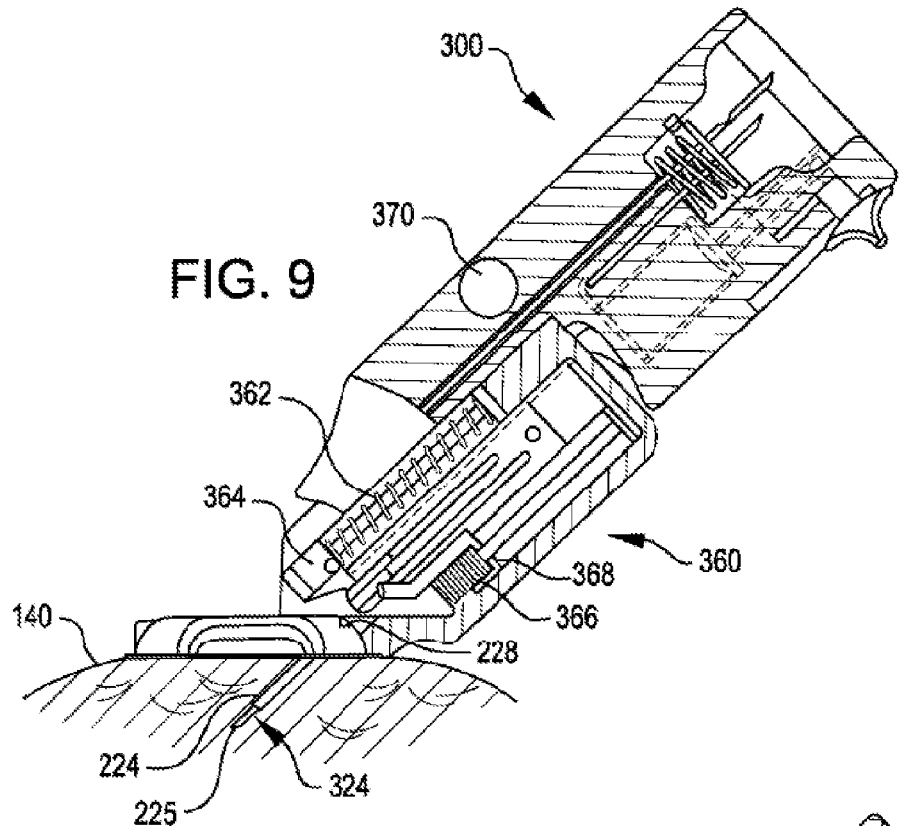
FIG. 9 is a side view, with portions cut away, of the service device of FIG. 4 after the cannula driver has driven a cannula carried on an inner needle to a cannula deployment position.

FIG. 9 shows the driver 360 after the cannula/needle assemble 324 have been driven through the port septum 228 and the infusion device 210 to beneath the patient's skin 140. It will be noted that the first spring 362 has been released and that the follower 364 is at the end of its travel. The second spring 366 may now be released to withdraw the needle 225 from the cannula 224.

Figure 10:
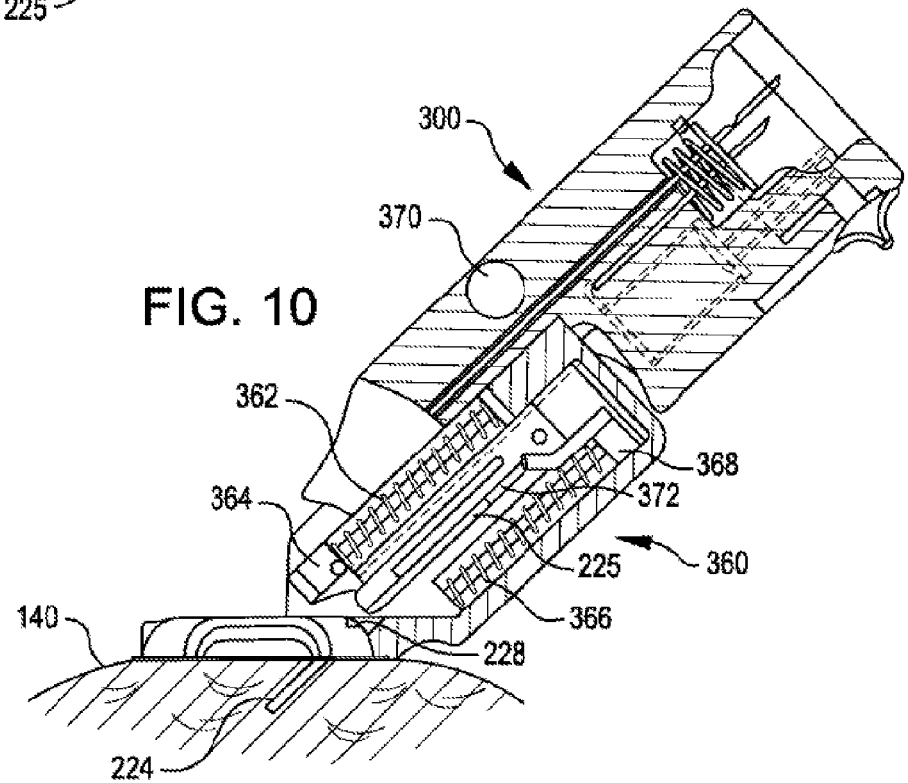
FIG. 10 is a side view, with portions cut away, of the service device of FIG. 4 after the cannula driver has withdrawn the needle upon which the cannula was driven from the cannula leaving the cannula behind in a deployed position.

FIG. 10 shows the driver 360 after the needle has been withdrawn from the cannula 224. The needle 225 has been withdrawn back out of the infusion device 210, through the port septum 228, and into a cavity 372 within the driver 360. Hence, it will be noted that the second spring 366 has been released and that the follower 368 is at the end of its travel. With the needle 225 withdrawn from the cannula 224, the cannula 224 is left in its deployed position beneath the skin 140 of the patient while the needle 225 is safely stored in cavity 372 for sharps disposal.

Now that the cannula 224 is deployed, the service device 300 may be removed from the infusion device 210. This is illustrated in FIG. 11. The service device 210 has been removed and separated from the infusion device 210. The infusion device 210 remains adhered to the patient's skin 140 for delivering the liquid medicant, such as insulin, to the patient through the cannula 224. The service device 300 may be thrown away.

While particular embodiments of the present invention have been shown and described, modifications may be made, and it is therefore intended in the appended claims to cover all such changes and modifications which fall within the true spirit and scope of the invention as defined by those claims.

What is claimed:

1. An infusion system comprising:
a disposable wearable infusion device having a body arranged to be adhered to a patients skin, a port, and a reservoir for holding a liquid medicant to be infused into the patient; and
a filler device comprising a conduit for releasable attachment to the infusion device port, a cavity for receiving a vial of liquid medicant, a displaceable arm, and a pump for pumping an amount of air into the vial to displace from the vial a like amount of liquid medicant, wherein the quantity of air pumped into the vial depends on a length of travel of the displaceable arm.

2. The system of claim 1 wherein the infusion device includes a window through which the liquid medicant within the reservoir may be viewed.

3. The system of claim 1, wherein the filler device establishes fluid communication between the infusion device reservoir and the liquid medicant upon concurrently receiving the infusion device body and the vial of liquid medicant.

4. The system of claim 3, wherein the filler device is enabled to transfer a volume of the liquid medicant to the infusion device reservoir upon the cavity receiving the vial of the liquid medicant.

5. A filler device for filling a reservoir of a disposable wearable infusion device with a liquid medicant, comprising:
a body;
a cavity for receiving a vial of the liquid medicant;
a conduit for releasable attachment to a port of the infusion device and that establishes fluid communication between the infusion device reservoir and the liquid medicant;
a displaceable arm; and
a pump for pumping an amount of air into the vial to displace from the vial a like amount of liquid medicant to the infusion device reservoir.

6. The device of claim 5, wherein the pump is enabled to transfer the volume of the liquid medicant to the infusion device reservoir upon the cavity receiving the vial of the liquid medicant.

7. The device of claim 5, wherein the conduit establishes fluid communication between the infusion device reservoir and the liquid medicant upon the device concurrently receiving the infusion device and the vial of liquid medicant.

* * * * *